(12) United States Patent
Clemmons et al.

(10) Patent No.: US 8,834,381 B2
(45) Date of Patent: Sep. 16, 2014

(54) BLOOD PRESSURE CUFF APPARATUS AND SYSTEM

(71) Applicant: General Electric Company, Schenectady, NY (US)

(72) Inventors: John Clemmons, Tampa, FL (US); Bruce Arnold Friedman, Jasper, GA (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 13/721,339

(22) Filed: Dec. 20, 2012

(65) Prior Publication Data

US 2013/0116582 A1 May 9, 2013

Related U.S. Application Data

(63) Continuation of application No. 12/145,596, filed on Jun. 25, 2008.

(51) Int. Cl.
*A61B 5/02* (2006.01)

(52) U.S. Cl.
USPC ........................................ 600/499

(58) Field of Classification Search
USPC ................................. 600/490–499
See application file for complete search history.

(56) References Cited

U.S. PATENT DOCUMENTS

| 4,572,205 | A | 2/1986 | Sjonell |
| 5,660,182 | A | 8/1997 | Kuroshaki et al. |
| 5,931,790 | A | 8/1999 | Peel, III |
| 6,245,023 | B1 * | 6/2001 | Clemmons ............... 600/499 |
| 6,988,992 | B2 | 1/2006 | Just et al. |
| 7,166,077 | B2 * | 1/2007 | Millay et al. ............ 600/499 |
| 2005/0171445 | A1 | 8/2005 | Millay et al. |
| 2006/0167492 | A1 | 7/2006 | Prince |
| 2010/0137725 | A1 | 6/2010 | Takahashi et al. |

FOREIGN PATENT DOCUMENTS

| CN | 153125 A | 10/2004 |
| CN | 1732842 A | 2/2006 |
| JP | 60-92737 A | 5/1985 |
| JP | 02-107226 A | 4/1990 |
| JP | 04-309329 A | 10/1992 |
| JP | 07-024304 U1 | 5/1995 |
| JP | 10-165378 A | 6/1998 |
| JP | 2001-78970 A | 3/2001 |

(Continued)

OTHER PUBLICATIONS

"Human blood pressure determination by sphygmomanometry" by Perloff et al., Journal of the American Heart Association, Circulation, 1993, vol. 88, pp. 2460-2470.*

(Continued)

*Primary Examiner* — Navin Natnithithadha
*Assistant Examiner* — Vasuda Ramachandran
(74) *Attorney, Agent, or Firm* — Andrus Intellectual Property Law, LLP

(57) ABSTRACT

A pressure cuff is disclosed herein. The pressure cuff includes a sleeve and a cuff bladder. The cuff bladder defines a bladder length of 9.2+/−2.1 centimeters and a bladder width of 24.6+/−4.2 centimeters. The bladder length and bladder width dimensions provide precise non-invasive blood pressure measurements when the pressure cuff is applied to a forearm having a circumference in the range of 27 to 37 centimeters.

7 Claims, 2 Drawing Sheets

(56) References Cited

FOREIGN PATENT DOCUMENTS

| | | | |
|---|---|---|---|
| JP | 2001-506167 | A | 5/2001 |
| JP | 2002-238864 | A | 8/2002 |
| JP | 2006-075436 | A | 3/2006 |
| JP | 2006-247216 | A | 9/2006 |
| JP | 2008-86713 | A | 4/2008 |

OTHER PUBLICATIONS

Patent Abstracts of Japan, Terumo Corp., Publ. No. 2006-075436, Mar. 23, 2006.
Patent Abstracts of Japan, Omnicuff SA, Publ. No. 04-309329, Oct. 30, 1992.
Patent Abstracts of Japan, Fukuda Denshi Co Ltd., Publ. No. 10-165378, Jun. 23, 1998.
Patent Abstracts of Japan, Matsushita Electric Works Ltd., Publ. No. 02-107226, Apr. 19, 1990.
Japanese Office Action (TPO-6688) dated Jun. 4, 2013.
Patent Abstracts of Japan—Publication No. 2006-247216, Sep. 21, 2006.
Patent Abstracts of Japan, Terumo Corp., Publ. No. 2002-238864, Aug. 27, 2002.
Chinese Office Action dated Jul. 9, 2012.
Chinese Search Report, Jun. 25, 2009.

* cited by examiner

US 8,834,381 B2

BLOOD PRESSURE CUFF APPARATUS AND SYSTEM

CROSS REFERENCE TO RELATED APPLICATION

The present application is a continuation of U.S. patent application Ser. No. 12/145,596, filed Jun. 25, 2008.

BACKGROUND OF THE INVENTION

The subject matter disclosed herein relates to a blood pressure cuff apparatus adapted for use on a patient's forearm, and a system comprising the blood pressure cuff apparatus.

Conventional non-invasive blood pressure (NIBP) monitoring systems generally inflate a pressure cuff above the patient's systolic pressure and measure oscillations in the cuff as the cuff is deflated. The pressure cuff is wrapped around the patient's upper arm and secured thereto with a fastening mechanism such as, for example, a hook and loop fastening mechanism. After wrapping and securing the pressure cuff, a cuff bladder is inflated with air to apply a variable amount of pressure. In order to maximize the precision with which a NIBP monitoring system estimates a given patient's blood pressure, the pressure cuff must be properly sized relative to the patient's upper atm.

Conventional pressure cuffs and cuff bladders each comprise length and width dimensions that define a generally rectangular shape. The pressure cuffs are sized by selecting length and width cuff bladder dimensions in proportion to a target patient's upper arm circumference. One problem is that the upper arm circumference of an obese patient becomes so large that it is difficult to properly fit. More precisely, in order to maintain the desired proportionality, the width of the pressure cuff becomes so large that it extends from the upper arm beyond the patient's elbow. When a pressure cuff is applied in this manner, the accuracy of the resultant blood pressure estimate is potentially greatly diminished. Another problem is that subcutaneous adipose tissue in the upper arm of an obese patient can interfere with NIBP measurements thereby potentially introducing a source of error.

BRIEF DESCRIPTION OF THE INVENTION

The above-mentioned shortcomings, disadvantages and problems are addressed herein which will be understood by reading and understanding the following specification.

In an embodiment, a pressure cuff includes a sleeve and a cuff bladder. The cuff bladder defines a bladder width of 9.2+/−2.1 centimeters and a bladder length of 24.6+/−4.2 centimeters. The bladder length and bladder width dimensions provide precise non-invasive blood pressure measurements when the pressure cuff is applied to a forearm having a circumference in the range of 27 to 37 centimeters.

In another embodiment, a pressure cuff includes a sleeve and a cuff bladder. The cuff bladder defines a width ratio range of 0.25 to 0.34 and a length ratio range of 0.66 to 0.91. The bladder length ratio range and bladder width ratio range provide optimal non-invasive blood pressure measurement precision when the pressure cuff is applied to a patient's forearm.

In another embodiment, a system includes a blood pressure monitor, and a pressure cuff pneumatically coupled with the blood pressure monitor. The pressure cuff includes a sleeve and a cuff bladder retained by the sleeve. The cuff bladder comprises a bladder width of 9.2+/−2.1 centimeters and a bladder length of 24.6+/−4.2 centimeters. The bladder length and bladder width dimensions provide precise non-invasive blood pressure measurements when the pressure cuff is applied to a forearm having a circumference in the range of 27 to 37 centimeters.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
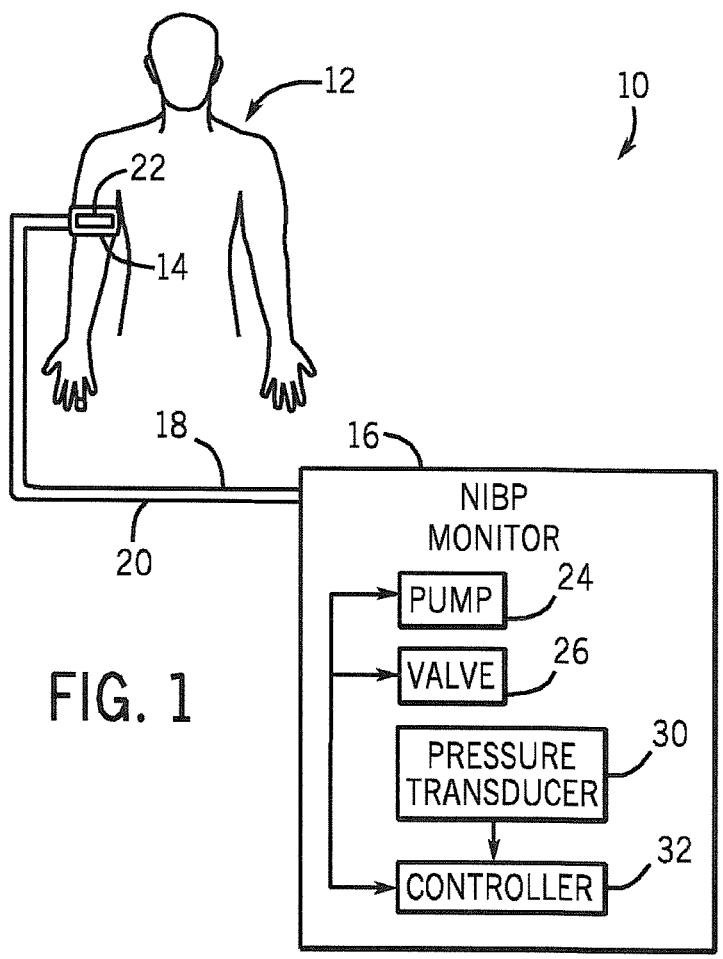
FIG. 1 is a schematic diagram of a non-invasive blood pressure monitoring system attached to a patient in accordance with an embodiment.

Referring to FIG. 1, a non-invasive blood pressure (NIBP) monitoring system 10 attached to a patient 12 is shown in accordance with an embodiment. The NIBP monitoring system 10 includes a pressure cuff 14 pneumatically coupled with a NIBP monitor 16 via the flexible tubes 18, 20. The pressure cuff 14 includes a cuff bladder 22. For purposes of this disclosure, the term bladder should be defined to include an inflatable pocket or chamber. The NIBP monitor 16 includes a pump 24 adapted to inflate the cuff bladder 22, and one or more valves 26 adapted to deflate the cuff bladder 22. The NIBP monitor 16 also includes a pressure transducer 30 operable to sense or identify pressure pulses at the portion of the limb to which the pressure cuff 14 is attached. A controller 32 converts the pressure pulse data from the pressure transducer 30 into blood pressure data in a known manner.

The NIBP monitor 16 is configured to measure mean arterial pressure (MAP), systolic blood pressure (SYS), and/or diastolic blood pressure (DIA) by inflating the pressure cuff 14 to a supra-systolic pressure level and measuring oscillations under the cuff 14 as the cuff 14 is deflated. For purposes of this disclosure, the term "oscillation" refers to a measurable pressure level pulse produced by a change in volume of an artery under the pressure cuff 14.

There are several problems with implementing an upper arm pressure cuff on an obese patient as will be described in detail hereinafter. For purposes of this disclosure, the term "obese" should be defined to include a body mass index (BMI) within the range of 30 to 40. The term body mass index refers to a patient's weight divided by the square of their height (BMI=weight/height$^2$). A first problem with implementing an upper arm pressure cuff on an obese patient is related to the fact that upper arm circumference tends to increase as BMI increases. Accordingly, an upper arm cuff geometry adapted to accommodate an obese patient's upper arm circumference may be constrained by the length of the upper arm or extend beyond the elbow. A second problem with implementing an upper arm pressure cuff on an obese patient is related to the fact that the upper arm of an obese patient can include excess subcutaneous adipose tissue that can interfere with NIBP measurement precision.

As a solution to the previously described problems, the pressure cuff 14 is adapted for use on a patient's forearm rather than their upper arm. For purposes of a NIBP acquisition site, the forearm provides several advantages over the upper arm including the following: the forearm has a smaller range of circumferential variation among patients; and generally includes less subcutaneous adipose tissue. Accordingly, the pressure cuff 14 enables the precise NIBP measurement of patients for whom conventional upper arm cuffs are not well suited such as, for example, obese patients or muscular patients with highly developed upper arms.

Pressure cuffs adapted for use on a patient's upper arm are generally sized by selecting length and width cuff bladder dimension in proportion to the target patient's upper arm circumference. This cuff geometry proportionality will hereinafter be described in terms of a width ratio defined as bladder width divided by target limb circumference, and a length ratio defined as bladder length divided by target limb circumference.

As an example, a pressure cuff with a 14.25 centimeter bladder width and a 27.75 centimeter bladder length is appropriately sized for a patient having an upper a in circumference in the range of 23.0 to 33.0 centimeters. As another example, a pressure cuff with a 17.50 centimeter bladder width and a 33.00 centimeter bladder length is appropriately sized for a larger patient having an upper arm circumference in the range of 31.0 to 40.0 centimeters. As yet another example, a pressure cuff with a 21.25 centimeter bladder width and a 40.00 centimeter bladder length is appropriately sized for an even larger patient having an upper arm circumference in the range of 38.0 to 50.0 centimeters. The first exemplary pressure cuff would yield a width ratio range of 0.43 to 0.62 and a length ratio range of 0.84 to 1.21, the second exemplary pressure cuff would yield a width ratio range of 0.44 to 0.56 and a length ratio range of 0.83 to 1.06, and the third exemplary pressure cuff would yield a width ratio range of 0.43 to 0.56 and a length ratio range of 0.80 to 1.05. The previously described length and width ratios have been determined empirically over time to improve the precision of upper arm NIBP measurements and are well known to those skilled in the art.

Initial experiments conducted using upper arm cuffs on the forearm resulted in BP measurements that were in error by 11.5 mmHg for systolic and 8.2 mmHg for diastolic when compared to invasive pressure measurements. As is known to those skilled in the art, invasive blood pressure measurements are directly acquired from within the patient's vascular system such as with a catheter, and are generally regarded as the most accurate means for measuring blood pressure. These results indicated that the width and length ratios commonly used for upper arm cuffs could not be applied to blood pressure measurements on the forearm.

Research was conducted to identify other cuff bladder geometries that may yield more accurate results when applied to the forearm. More precisely, a design of experiments was performed using a variety of different cuff bladder sizes and shapes in order to correlate forearm cuff bladder geometry with resultant NIBP measurement precision. The precision of the NIBP measurements acquired using a forearm pressure cuff was established relative to invasively acquired blood pressure measurements. Blood pressures in peripheral vessels such as the radial artery differ from central blood pressures. These differences are due to reflections from the peripheral vascular bed.

The design of experiments indicated that a pressure cuff comprising a cuff bladder having a 9.2 centimeter width and a 24.6 centimeter length yielded a high degree of precision when applied to a patient having a forearm circumference in the range of 27 to 37 centimeters. In order to maintain consistency, the circumference of the forearm was measured at a point one centimeter below the medial crease of the elbow. The 27 to 37 centimeter forearm circumference range was selected to include a high percentage of obese patients, however, this circumference range may also include forearm circumferences of patients falling within other patient BMI ranges. Therefore, although the pressure cuff 14 is particularly well adapted for use with obese patients having a forearm circumference in the range of 27 to 37 centimeters, it should be appreciated that the pressure cuff 14 may also be appropriate for other patient BMI ranges and other forearm circumference ranges.

The forearm pressure cuff geometry identified by the design of experiments (i.e., 9.2 centimeter width and a 24.6 centimeter length) yields a width ratio range of 0.25 to 0.34 and a length ratio range of 0.66 to 0.91. This forearm pressure cuff geometry identified by the design of experiments comprises very different width ratio ranges and length ratio ranges, and provides greatly improved NIBP measurement precision, as compared to conventional upper arm cuff geometries applied to the forearm. It should therefore be appreciated that by conducting the design of experiments and identifying specific optimized cuff dimensions for a range of forearm circumferences, it is now possible to non-invasively measure the blood pressure of obese patients with a high degree of precision.

The design of experiments also indicated that a cuff bladder having a width variation of +/−2.1 centimeters and a length variation of +/−4.2 centimeters yields an adequate degree of precision when applied to a patient having a forearm circumference in the range of 27 to 37 centimeters. Accordingly, based on the results of the design of experiments, a pressure cuff bladder comprising a 9.2+/−2.1 centimeter width and a 24.6+/−4.2 centimeter length should be considered to be optimized for purposes of obtaining a precise NIBP measurement when applied to a patient having a forearm circumference in the range of 27 to 37 centimeters.

Figure 2:
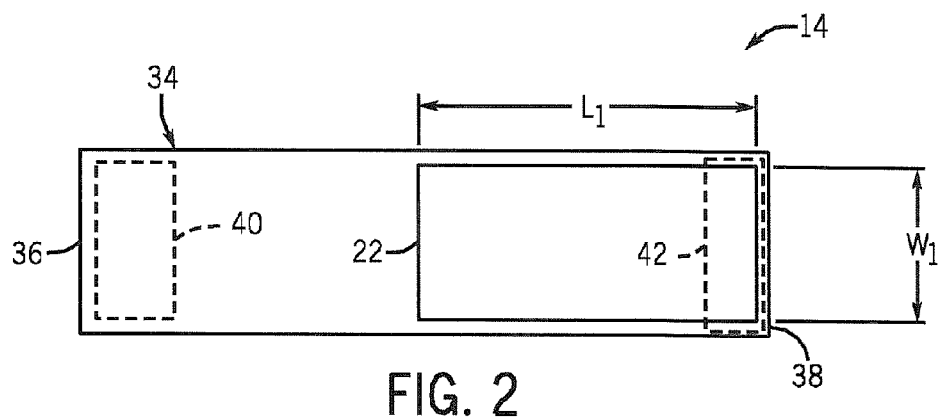
FIG. 2 is a schematic diagram of a pressure cuff in accordance with an embodiment.

Referring to FIG. 2, a schematic illustration of the pressure cuff 14 is shown in accordance with an embodiment. The pressure cuff 14 comprises a flexible, non-distensible sleeve 34 and the cuff bladder 22. The sleeve 34 is flexible such that it may be conveniently wrapped around a patient's limb, and non-distensible such that it generally does not expand or swell in response to pressure. According to one embodiment, the sleeve 34 comprises two or more layers that are impermeable to air and are fused together near their peripheral edges in a manner adapted to form the cuff bladder 22. According to another embodiment, the cuff bladder 22 is a separate component retained by the sleeve 34. The sleeve 34 is generally rectangular defining a sleeve end 36 and a generally opposite sleeve end 38. The cuff bladder 22 is also generally rectangular, and defines a bladder length $L_1$ and a bladder width $W_1$.

The sleeve 34 is preferably long enough to be wrapped around a patient's forearm such that the sleeve ends 36, 38 overlap each other by an amount necessary to secure the pressure cuff 14. According to one embodiment, the sleeve 34 comprises complementary hook and loop type fastening portions 40, 42 adapted to retain the pressure cuff 14 on the patient's forearm. As previously described, based on the results of the design of experiments, the bladder width $W_1$ is 9.2+/−2.1 centimeters and the bladder length $L_1$ is 24.6+/−4.2 centimeters such that optimal NIBP measurement precision is maintained when the pressure cuff 14 is applied to a patient having a forearm circumference in the range of 27 to 37 centimeters.

Figure 3:
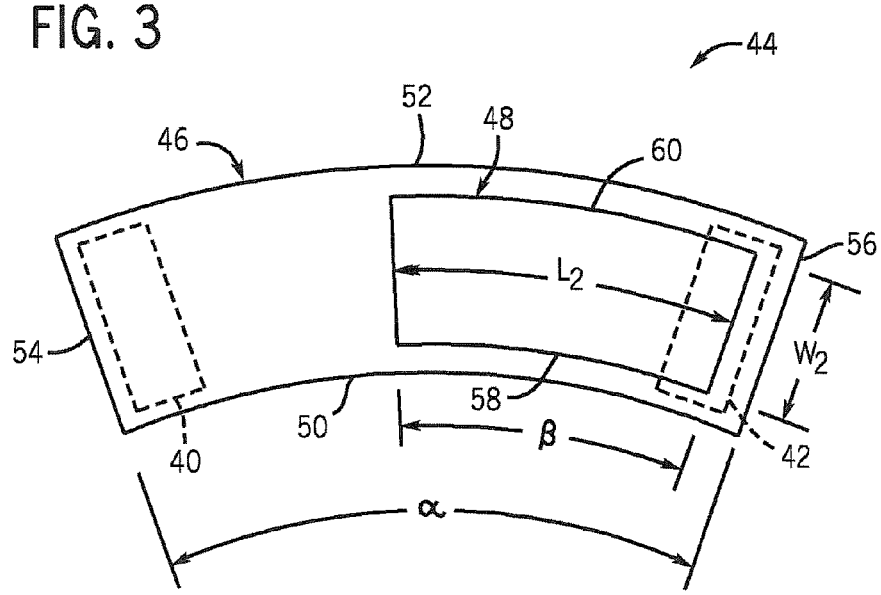
FIG. 3 is a schematic diagram of a pressure cuff in accordance with another embodiment.

Referring to FIG. 3, a schematic illustration of a pressure cuff 44 is shown in accordance with an embodiment. The pressure cuff 44 comprises a flexible, non-distensible sleeve 46 and a cuff bladder 48. The sleeve 46 is flexible such that it may be conveniently wrapped around a patient's limb, and non-distensible such that it generally does not expand or swell in response to pressure. According to one embodiment, the sleeve 46 comprises two or more layers that are impermeable to air and are fused together near their peripheral edges in a manner adapted to form the cuff bladder 48. According to another embodiment, the cuff bladder 48 is a separate component retained by the sleeve 46.

The sleeve 46 is generally arcuate shaped, and comprises radial inner and outer edges 50, 52 that define an angle α. The sleeve 46 also comprises a sleeve end 54 and a generally opposite sleeve end 56. The cuff bladder 48 is generally arcuate shaped, and comprises radial inner and outer edges 58, 60 that define an angle β. The cuff bladder 48 defines a bladder length $L_2$ and a bladder width $W_2$. According to one embodiment, angle α is approximately 48.1 degrees, and the angle β is approximately 23.4. As shown in FIG. 3, the bladder length $L_2$ is defined at the middle of the bladder 48 as measured along the bladder width $W_2$.

The generally arc shape of the sleeve 46 forms a generally conical shape when the sleeve ends 54 and 56 are engaged in the manner described hereinabove with respect to the pressure cuff 14 (shown in FIG. 2). This conical shape conforms more closely to that of a typical obese patient's forearm and may therefore provide a better fit. As previously described, based on the results of the design of experiments, the bladder width $W_2$ is 9.2+/−2.1 centimeters and the bladder length $L_2$ is 24.6+/−4.2 centimeters such that optimal NIBP measurement precision is maintained when the pressure cuff 44 is applied to a patient having a forearm circumference in the range of 27 to 37 centimeters.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. A method of monitoring the blood pressure of a patient having a forearm circumference in the range of 27 to 37 centimeters using a noninvasive blood pressure (NIBP) monitor, comprising:
    providing a pressure cuff having a bladder having a width ratio range of 0.25 to 0.34 and a length ratio range of 0.66 to 0.91;
    positioning the pressure cuff around the forearm of the patient; and
    selectively inflating and deflating the pressure cuff using the NIBP monitor to non-invasively monitor the blood pressure of the patient while the pressure cuff is around the forearm of the patient.

2. The method of claim 1 wherein the bladder is generally arcuate shaped.

3. The method of claim 2 wherein the generally arcuate shaped cuff bladder includes radial inner and outer edges each extending along an angle in the range of 20 to 26 degrees.

4. The method of claim 2 wherein the generally arcuate shaped cuff bladder includes radial inner and outer edges each extending along an angle of approximately 23 degrees.

5. The method of claim 1 wherein the cuff bladder comprises a width of 9.2+/−2.1 centimeters and a length of 24.6+/−4.2 centimeters.

6. The method of claim 2 wherein the generally arcuate shaped cuff bladder comprises a width of 9.2+/−2.1 centimeters and a length of 24.6+/−4.2 centimeters.

7. The method of claim 1, wherein the pressure cuff includes a sleeve that receives the bladder, wherein the sleeve includes radial inner and outer edges each extending over an angle of approximately 48 degrees.

* * * * *